US00PP16868P2

(12) United States Plant Patent
Arimitsu

(10) Patent No.: US PP16,868 P2
(45) Date of Patent: Jul. 25, 2006

(54) ***PORTULACA* PLANT NAMED 'BODHIGYEL'**

(50) Latin Name: *Portulaca grandiflora*
Varietal Denomination: Bodhigyel

(75) Inventor: Yoshiro Arimitsu, Lompoc, CA (US)

(73) Assignee: John Bodger & Son Co., South El Monte, CA (US)

( * ) Notice: Subject to any disclaimer, the term of this patent is extended or adjusted under 35 U.S.C. 154(b) by 6 days.

(21) Appl. No.: 11/091,805

(22) Filed: Mar. 28, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Portulaca* plant named 'Bodhigyel', characterized by its upright, low spreading and mounded plant habit; freely branching and vigorous growth habit; dense and bushy growth habit; freely and continuous flowering habit; large double bright yellow-colored flowers; and no pollen production.

1 Drawing Sheet

Botanical designation: *Portulaca grandiflora.*
Cultivar denomination: 'Bodhigyel'.

BACKGROUND OF THE INVENTION

The present Invention relates to a new and distinct cultivar of *Portulaca* plant, botanically known as *Portulaca grandiflora,* and hereinafter referred to by the cultivar name Bodhigyel.

The new *Portulaca* is a product of a planned breeding program conducted by the Inventor in Lompoc, Calif. The objective of the breeding program is to create new *Portulacas* with dense plant habit, numerous large flowers and attractive flower coloration.

The new *Portulaca* originated from a cross-pollination made by the Inventor in May, 2001, of the seed-propagated *Portulaca grandiflora* cultivar Sundial Mango, not patented, as the female, or seed, parent with the seed-propagated *Portulaca grandiflora* cultivar Sundial Pink, not patented, as the male, or pollen, parent. The new *Portulaca* was selected as a single plant from the resulting progeny of the stated cross-pollination by the Inventor in a controlled environment in Lompoc, Calif. in April, 2003.

Asexual reproduction of the new cultivar by vegetative cuttings in Lompoc, Calif. since April, 2003 has shown that the unique features of this new *Portulaca* are stable and reproduced true to type in successive generations.

SUMMARY OF THE INVENTION

Plants of the cultivar Bodhigyel have not been observed under all possible environmental conditions. The phenotype may vary somewhat with variations in environment such as temperature and light intensity without, however, any variance in genotype.

The following traits have been repeatedly observed and are determined to be the unique characteristics of 'Bodhigyel'. These characteristics in combination distinguish 'Bodhigyel' as a new and distinct cultivar:

1. Upright, low spreading and mounded plant habit.

2. Freely branching and vigorous growth habit; dense and bushy growth habit.
3. Freely and continuous flowering habit.
4. Large double bright yellow-colored flowers.
5. No pollen production.

Plants of the new *Portulaca* differ from plants of the parents, the cultivars Sundial Mango and Sundial Pink, in the following characteristics:

1. Plants of the new *Portulaca* have a denser growth habit than plants of the cultivars Sundial Mango and Sundial Pink.
2. Plants of the new *Portulaca* flower continuously whereas plants of the cultivars Sundial Mango and Sundial Pink flower intermittently.
3. Flowers of plants of the new *Portulaca* do not produce pollen whereas flowers of plants of the cultivars Sundial Mango and Sundial Pink produce pollen.
4. Plants of the new *Portulaca* and the cultivars Sundial Mango and Sundial Pink differ in flower coloration.

Plants of the new *Portulaca* can be compared to plants of the seed-propagated *Portulaca grandiflora* cultivar Sundial Gold, not patented. In side-by-side comparisons conducted in Lompoc, Calif., plants of the new *Portulaca* differed from plants of the cultivar Sundial Gold in the following characteristics:

1. Plants of the new *Portulaca* had a denser growth habit than plants of the cultivar Sundial Gold.
2. Plants of the new *Portulaca* flowered continuously whereas plants of the cultivar Sundial Gold flowered intermittently.
3. Flowers of plants of the new *Portulaca* did not produce pollen whereas flowers of plants of the cultivar Sundial Gold produced pollen.

Plants of the new *Portulaca* can be compared to plants of the seed-propagated *Portulaca grandiflora* cultivar Margarita Banana, not patented. In side-by-side comparisons conducted in Lompoc, Calif., plants of the new *Portulaca* differed from plants of the cultivar Margarita Banana in the following characteristics:

1. Plants of the new *Portulaca* were more vigorous than plants of the cultivar Margarita Banana.
2. Plants of the new *Portulaca* had larger flowers than plants of the cultivar Margarita Banana.
3. Flowers of plants of the new *Portulaca* did not produce pollen whereas flowers of plants of the cultivar Margarita Banana produced pollen.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Portulaca*.

The photograph at the bottom of the sheet comprises a side perspective view of a typical flowering plant of 'Bodhigyel' grown in a container.

The photograph at the top of the sheet comprises a close-up view of typical flowers and leaves of 'Bodhigyel'.

DETAILED BOTANICAL DESCRIPTION

The aforementioned photographs and following observations and measurements describe plants grown in Lompoc, Calif., under commercial practice during the winter and early spring in a polycarbonate-covered greenhouse with day temperatures about 21 to 24° C., night temperatures about 16 to 18° C. and light levels about 5,000 to 9,000 foot-candles. Plants were grown with one rooted cutting per 10-cm container for about 13 weeks. In the following description, color references are made to The Royal Horticultural Society Colour Chart, 1995 Edition, except where general terms of ordinary dictionary significance are used.

Botanical classification: *Portulaca grandiflora* cultivar Bodhigyel.

Parentage:

*Female parent.*—*Portulaca grandiflora* cultivar Sundial Mango, not patented.

*Male parent.*—*Portulaca grandiflora* cultivar Sundial Pink, not patented.

Propagation:

*Type cuttings.*—Vegetative cuttings.

*Time to initiate roots.*—About 7 to 10 days at 24° C.

*Time to produce a rooted young plant.*—About two to three weeks at 24° C.

*Root description.*—Fine, fibrous, whitish in color.

*Rooting habit.*—Freely branching.

Plant description:

*Plant and growth habit.*—Annual flowering plant; upright, low spreading and mounded plant habit. Vigorous and freely branching growth habit with about four primary branches per plant and secondary laterals developing at every node; dense and bushy growth habit.

*Plant height.*—About 7 cm.

*Plant diameter.*—About 27 cm.

*Lateral branches.*—Length: About 25 cm. Diameter: About 4 mm. Internode length: About 2.8 cm. Texture: Mostly smooth; bristle-like pubescence at nodes; succulent. Color: 177A tinged with 194A.

*Foliage description.*—Arrangement: Alternate or whorled, simple. Length: About 1.6 cm. Width: About 4 mm. Shape: Acicular. Apex: Acute. Base: Attenuate. Margin: Entire. Texture, upper and lower surfaces: Smooth, glabrous; succulent. Venation pattern: Parallel; reticulate. Color: Developing foliage, upper and lower surfaces: 146A. Fully expanded foliage, upper and lower surfaces: 146A. Venation, upper and lower surfaces: 146A. Petiole length: About 1 mm. Petiole diameter: About 1 mm. Petiole color: 146D.

Flower description:

*Flower type and habit.*—Large double radial cup-shaped flowers; flowers face upward or outward; two to three flowers per terminal or axil. Flowers persistent. Freely flowering habit, typically about 75 open flowers and flower buds per plant. Flowers sessile.

*Natural flowering season.*—Spring until frost in the autumn; flowering continuous during the flowering period.

*Flower longevity on the plant.*—About three to five days.

*Fragrance.*—None detected.

*Flower diameter.*—Large, about 5 cm.

*Flower depth (height).*—About 2 cm.

*Flower buds.*—Length: About 1.2 cm. Diameter: About 7 mm. Shape: Ovoid. Color: 147C; towards the base, tinged with 178B.

*Petals.*—Arrangement/appearance: About 30 petals arranged in about seven whorls; petals imbricate. Length: About 2.2 cm. Width: About 2 cm. Shape: Cordate. Apex: Emarginate. Base: Attenuate. Margin: Entire. Texture, upper and lower surfaces: Smooth, glabrous; satiny. Color: When opening, upper and lower surfaces: 12A. Fully opened, upper surface: Towards the apex, 12B; towards the base, 5A; at the base, 178D. Fully opened, lower surface: 12B.

*Sepals.*—Quantity/arrangement: Two per flower; opposite. Length: About 1 cm. Width: About 9 mm. Shape: Elliptic. Apex: Acute. Base: Truncate. Margin: Entire. Texture, upper and lower surfaces: Smooth, glabrous. Color, immature and mature, upper surface: 147C. Color, immature and mature, lower surface: 147C; towards the base, tinged with 178A.

*Reproductive organs.*—Stamens: Quantity per flower: About 200. Anther shape: Oblong. Anther length: Less than 1 mm. Anther color: 34A. Pollen amount: None observed. Pistils: Quantity per flower: One. Pistil length: About 1.4 cm. Stigma shape: Ten-parted. Stigma color: 34D. Style length: About 7 mm. Style color: 34B. Ovary color: 145D tinged with 173D.

*Fruit/seed.*—Fruit and seed production has not been observed.

Disease/pest resistance: Plants of the new *Portulaca* have not been noted to be resistant to pathogens and pests common to *Portulaca*.

It is claimed:

1. A new and distinct cultivar of *Portulaca* plant named 'Bodhigyel', as illustrated and described.

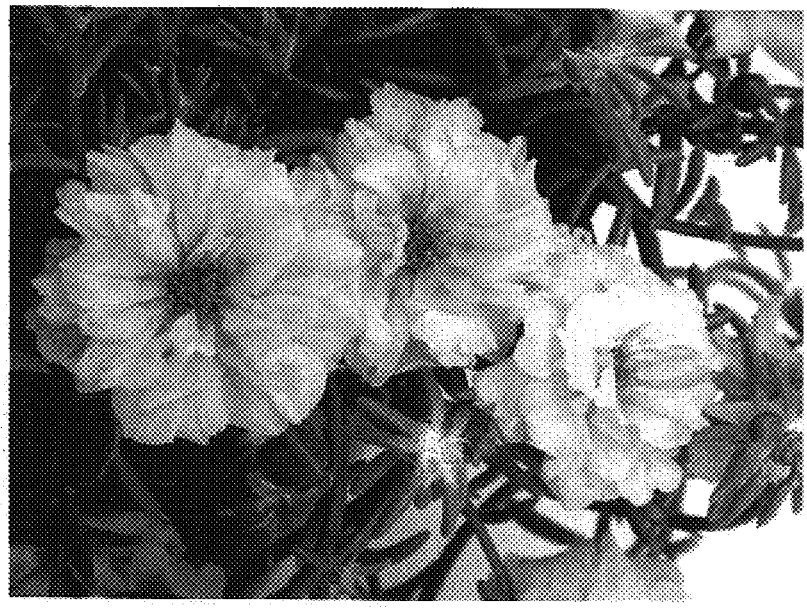
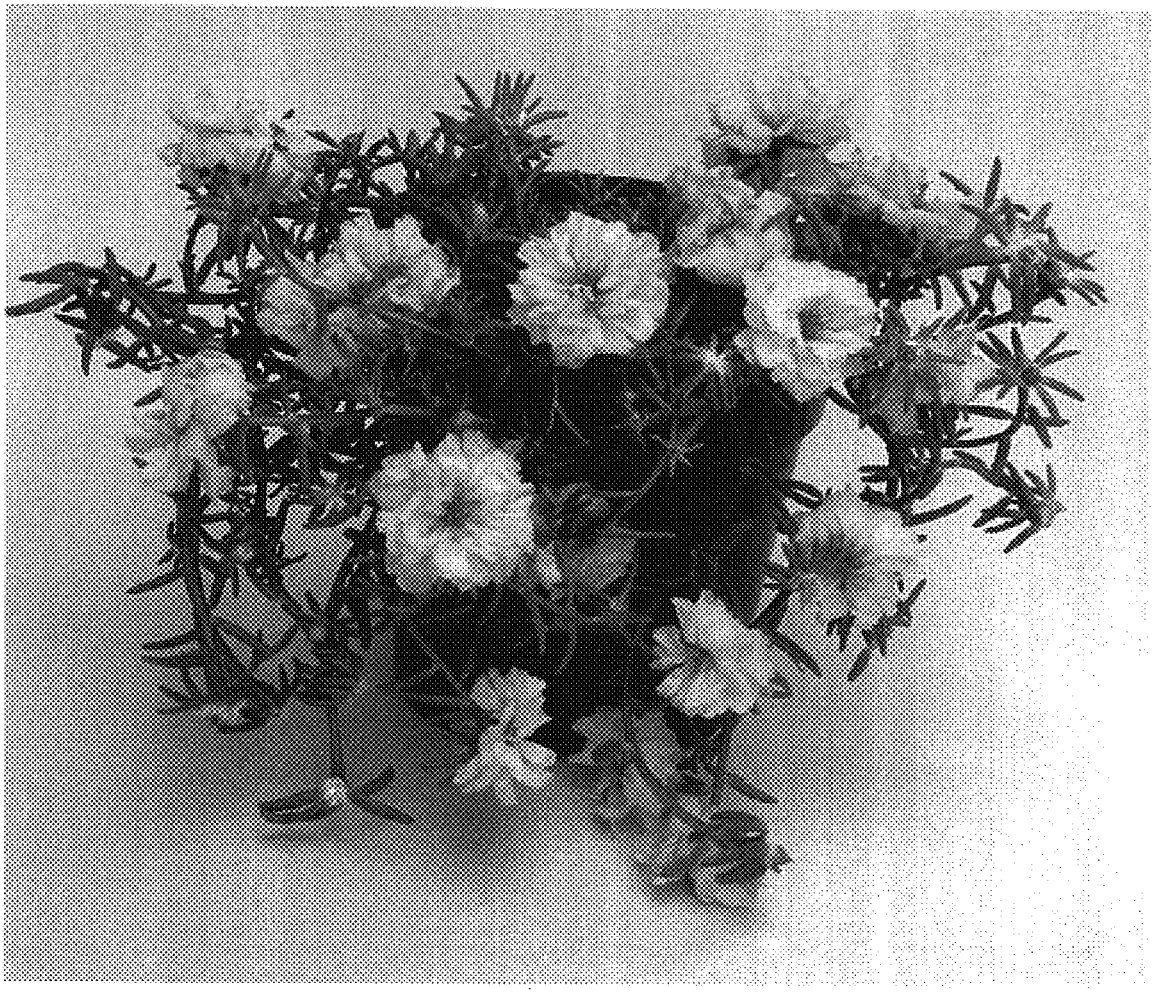

* * * * *